US006496258B1

(12) United States Patent
Leipertz et al.

(10) Patent No.: US 6,496,258 B1
(45) Date of Patent: Dec. 17, 2002

(54) DEVICE AND METHOD FOR SIMULTANEOUS IN-SITU DETERMINATION OF PARTICLE SIZE AND MASS CONCENTRATION OF FLUID-BORNE PARTICLES

(75) Inventors: Alfred Leipertz, Erlangen (DE); Stefan Will, Nürnberg (DE); Stephan Schraml, Fürth (DE)

(73) Assignee: Esytec Energie-und Systemtechnik GmbH, Erlangen (DE)

(*) Notice: Subject to any disclaimer, the term of this patent is extended or adjusted under 35 U.S.C. 154(b) by 0 days.

(21) Appl. No.: 09/869,318

(22) PCT Filed: Feb. 1, 2000

(86) PCT No.: PCT/EP00/00781

§ 371 (c)(1),
(2), (4) Date: Jul. 24, 2001

(87) PCT Pub. No.: WO00/52449

PCT Pub. Date: Sep. 8, 2000

(30) Foreign Application Priority Data

Mar. 2, 1999 (DE) .......................................... 199 04 691

(51) Int. Cl.[7] .............................................. G01N 21/49
(52) U.S. Cl. ........................ 356/336; 356/338; 356/340; 356/343
(58) Field of Search ................................ 356/336, 337, 356/338, 339, 340, 341, 342, 343; 250/574, 573, 575

(56) References Cited

U.S. PATENT DOCUMENTS

| 4,415,265 A | 11/1983 | Campillo et al. |
| 4,429,995 A | 2/1984 | Goulas |
| 4,486,535 A | 12/1984 | Dimpfl |
| 4,605,535 A | 8/1986 | Dimpfl |
| 4,966,462 A | * 10/1990 | Novick ........................ 356/437 |
| 5,180,921 A | 1/1993 | Moreau et al. |
| 5,285,467 A | 2/1994 | Scheps |
| 5,316,983 A | 5/1994 | Fujimori et al. |
| 5,815,264 A | 9/1998 | Reed et al. |
| 5,920,388 A | 7/1999 | Sandberg et al. |
| 6,181,419 B1 | 1/2001 | Snelling et al. |

FOREIGN PATENT DOCUMENTS

| DE | 19606005 | 4/1997 |
| EP | 837316 | 4/1998 |
| JP | 8-094526 | 4/1996 |
| WO | 97/30335 | 8/1997 |

OTHER PUBLICATIONS

J.A. Pinson, D.L. Mitchell, R.J. Santoro, and T.A. Litzinger, SAE Technical Paper Series 932650, Society of Automotive Engineers, Warrendale, PA, 1993.
S. Will, Schraml and A. Leipertz, 26th, Symposium (International) on Combustion (The Combustion Institute, Pittsburg, PA., 1996), 2277–2284.
B. Quay, T.–W. Lee, T. Ni, and R.J. Santoro, Combustion and Flame 97, S. 384–3922, 1994.
English Language abstract of JP–8–094526.
Article titled Soot Diagnostics Using Laser–Induced Incandecence in Flames and Exhaust Flows, by R.T. Wainner et al., 1999 (A1AA–99–0640).

* cited by examiner

Primary Examiner—Hoa Q. Pham
(74) Attorney, Agent, or Firm—Greenblum & Bernstein, P.L.C.

(57) ABSTRACT

Method and device for simultaneous in-situ determination of particle size and mass concentration of fluid-borne particles, wherein the device includes a sensor unit comprising a sending unit and a receiver, a laser coupled to the sensor unit, a detector coupled to the sensor unit, and a microprocessor coupled to the sensor unit, wherein the sensor unit is at least one of adjustable in cross section and variable in diameter and wherein the sensor unit is arranged to one of protrude into the fluid-borne particles and wrap around the fluid-borne particles. The method includes placing the sensor unit adjacent a pipe having a gas flow and simultaneously determining a particle size and a mass concentration of the fluid-borne particles in the gas flow.

28 Claims, 2 Drawing Sheets

DEVICE AND METHOD FOR SIMULTANEOUS IN-SITU DETERMINATION OF PARTICLE SIZE AND MASS CONCENTRATION OF FLUID-BORNE PARTICLES

CROSS-REFERENCE TO RELATED APPLICATIONS

The present application is a National Stage Application of International Application No. PCT/EP00/00781, filed Feb. 1, 2000. Further, the present application claims priority under 35 U.S.C. §119 of German Patent Application No. 199 04 691.3-52 filed on Feb. 5, 1999.

BACKGROUND OF THE INVENTION

1. Field of the Invention

The invention relates to an optoelectronic measuring device and a method for in-situ characterization of fluid-borne particles in the sub-micrometer size range.

2. Discussion of Background Information

A number of different methods are known and used for determining the particle quantities such as particle size and concentration. Optical methods and devices allow an in-situ determination of relevant quantities while conventional methods such as electron microscopy allow only an off-line and/or ex-situ characterization and usually require a partial suctioning of the gas flow. A known device (U.S. Pat. No. 5,815,264) allows, for instance, irradiation of the particles to be tested and imaging the elastic scattering on a two-dimensional optical detector. However, the geometrical, high-resolution imaging of the separate particles allows the determination of the particle sizes only as long as the particle size is within or above the range of the utilized radiation wave lengths. Furthermore, the process can only be used in a limited range of particle concentration because, on the one hand, the particles must be visually separable on the detector and, on the other hand, it must be ensured that at least one single particle is represented within the high enlargement to be realized and the accordingly small examination volume. Additional deficits result from the shallow focus of the optical imaging which can lead to different image scales for the various depths and, thus, to inaccuracies of the size determination.

Additionally, a device is known for determining the particle size which evaluates the emission of laser-induced plasma (U.S. Pat. No. 5,316,983). Here, the plasma emission is evaluated regarding its intensity, its spatial presence, and its time trajectory, as well as the amplitude of the sound waves induced thereby.

Another optical process that enables the determination of particle composition and particle size (European Patent EP 0 837 316 A2) by irradiating particles and subsequently evaluating the thermal radiation and the scattering inside of a laser resonator is based on the examination of the vaporizability, the determination of the particle temperature, and the ratio of elastic scattering and thermal radiation, and depends on the use of several different optical detector units and a geometrical arrangement that cannot be selected freely. Thus, resulting in a considerable constructive and technical expense which strongly limits the usability of the method and questions its economic value. An additional, principle disadvantage of an invasive method is caused in several particles being evaporated completely due to the laser impact and a subsequent physical and/or chemical analysis becoming impossible. The utilization of optical methods demands the optical accessibility of the test objects and thus relies on constructive modifications.

Several methods and devices are known for the determination of the aggregate size, for example, by means of combined measurements of scattering and extinction or the determination of elastic scattering at different angles (e.g., according to J. A. Pinson, D. L. Mitchell, R. J. Santoro, and T. A. Litzinger, SAE Technical Paper Series 932650, Society of Automotive Engineers, Warrendale, Pa., 1993), however, only one method exists for the primary particle size which enables the in-situ measuring of this quantity by evaluating the thermal particle radiation (German Patent DE 196 06 005). Common devices and methods for determining the particle concentration are usually based on the extenuation of light or the filtering and subsequent evaluation of the filter loading. Further, a method is known that allows the concentration measurement of carbon black by detecting Planck's heat radiation after laser excitement by means of a quick digital camera (Japanese Patent JP 08-094526A). However, the two-dimensional imaging method here is dependent on a perpendicular arrangement of the laser light sheet and the detector which causes a strong limitation of the usability within technical systems. No suitable in-situ methods have existed until now for the simultaneous determination of primary particle size and concentration.

The characterization of particles in the nano-scale within different technical and industrial systems are very important regarding the variety of objective configurations. For example, the industrial production of carbon black and other technical powders relies on suitable measurement methods for characterizing the product and allowing a specific processing control as well without affecting the process itself. The resulting requirements, such as a largely automated data entry and processing and the in-situ measuring of the quantities cannot be fulfilled by prior art without considerable constructive modifications of the test objects, in spite of its great technical importance.

SUMMARY OF THE INVENTION

The invention therefore provides a method and a measuring device which enables a simultaneous in-situ determination of primary particle size and mass concentration of various particles. The invention also provides a device for determining the mass concentration and/or the primary particle size which enable an easy application in different technical and industrial test objects even when an optical access is only possible from a single side.

According to the present invention, a sensor unit allows the simultaneous determination of the primary particle size and the mass concentration by evaluating the thermal radiation after a pulsed excitement. The thermal excitement can occur, e.g., by way of a high-energy laser pulse. Here, an advantageous embodiment uses short pulses with a pulse duration of about 10 ns and wave lengths in the visual range of the spectrum, such as the ones to be achieved with pulsed solid state lasers. The detection occurs, e.g., by a temporally high-resolution photo multiplier module after suitable spectral filtering, for instance, for suppressing disturbing radiation.

According to one aspect of the invention, sensor unit allows the excitement and detection by way of only one optical access which is particularly advantageous regarding optically dense media with strong absorbing characteristics and in test objects hard to access. A sufficiently strong signal can always be determined in the detection of backscattering in any optical density. Here, the spectral selection of the exciting radiation and the signal occurs by way of suitable dichroitic elements, such as mirrors with reflection and/or transmission ranges, dependent on wave lengths, outside of the test object or by way of a local separation of the rays, for instance, by a hole within a mirror reflecting entirely.

The invention also provides for a method that includes simultaneously determining the primary particle size and the mass concentration from the time signal trajectory following a thermal excitement requiring only one excitement impulse. Here, the simultaneous determination of the two quantities allows, in particular, the simultaneous evaluation of the primary particle number density as well.

Advantageous variants of the sensor unit and/or the method according to the invention are described herein. For example, the detection occurs advantageously by means of a sensor module which already integrates all essential optical and electronic components, such as imaging optics, spectral filtering, and voltage supply. This embodiment allows the adaptation of the sensor unit to the test object without any further adjustment expense in simultaneous utilization of fiberoptical components which has a deciding advantage with regard to the practical use and the maintenance expense of the device. Additional components that expand the possibilities for utilizing the device and/or enabling a more precise determination of the quantities, in particular such for simultaneously determining elastic scattering, for simultaneous measurement of transmissions, and a temperature sensor can be integrated. Here, the electric scattering signal allows the determination of an additional size parameter (aggregate size), with the temperature measurement, for instance, performed by way of a resistance thermometer or a thermocouple, being used for the exact evaluation of the primary particle size. An essential aspect of the invention is the determination of the necessary quantity (s) without or with only minor modifications of the test object. For example, the utilization of a suitable device with a variable diameter, in which all exciting and detecting components have already been applied, allows the quick adaptation to or into the exhaust stream of combustion systems, such as motors, without modification of the exhaust stream and the subsequent measuring of the parameters without any further adjustment expense. Thus, the utilization as a standard measuring technique for emission tests of serial vehicles becomes possible. The integration of simultaneous transmission measurements allows the calibration of the particle concentration.

The utilization of an analog-digital converter and of a micro processor expands the invention by an automated determination, storage, and processing of the measurement data and the resulting values, which allow direct processing adjustments, for example. This embodiment must be rendered advantageous because it requires no separate posterior evaluation and the device can also be operated by non-experts. The data processing for the process according to the invention includes the simultaneous determination of the mass concentration, the average primary particle size, and additional parameters of the corresponding distribution function by analyzing the time trajectory of the signal preferably with consideration of the fluid temperature. When including a measured temperature value which exceeds the precision of the approximate estimation a more precise evaluation of the primary particle size and/or additional parameters of the distribution function can be performed. This is based on the fact that the cooling progression depends on the temperature gradients of particles and fluid and, thus, the exact temperature measurement of this param-eter improves the precision of the measurement values. Corresponding theoretic models can be found, e.g., in S. Will, S. Schraml and A. Leipertz, 26th, Symposium (International) on Combustion (The Combustion Institute, Pittsburgh, Pa., 1996), 2277–2284. In one variant the process can be used such that a comparison of the complete signal curves is performed with a library of calculated curves.

Here, the use of a variant according to the invention is particularly advantageous for the practical embodiment in which a suitable library is created simultaneously with the evaluation. For determining the average primary particle size a signal decay time $\tau$ can be adjusted to the experimental signal trajectory, for example, in punctual measurements. At the presence of a non-monodisperse size distribution, for example, the complete particle size distribution function or additional parameters of the distribution, such as the width, can be reconstructed by fitting the superposition of several exponential functions. Simultaneously, the maximal signal value is evaluated for determining the volume and/or mass concentration with the ability to determine quantifying values by way of integrating the turbidity values. Here, a luminescence diode or a compact diode laser and a photo diode or a photo transistor are used in an opposing arrangement, for example. In another embodiment the radiation source used for exciting the thermal radiation can simultaneously be used for the transmission measurement. The process of the calibration, e.g., is described in S. Will, S. Schraml and A. Leipertz, 26th Symposium (International) on Combustion (The Combustion Institute, Pittsburgh, Pa., 1996), 2277–2284 as well.

Further, with the additional measuring of the elastic light scattering, such as to be performed with a sensor unit according to the invention can be provided that allows the simultaneous determination of the aggregate size as well using the maximal signal of the thermal radiation and the scattering signal. The determination of the elastic scattering occurs advantageously by using a narrow-band filter for spectral separation of disturbing signals adjusted to the wave length of the exciting light source. For determining the aggregate size the quotient of elastic distribution signal and maximal signal of the thermal signal is formed which is proportional to a higher power exponent of the aggregate diameter (B. Quay, T.-W. Lee, T. Ni and R. J. Santoro, Combustion and Flame 97, S. 384–3922, 1994).

The invention also provides for an optical sensor unit for simultaneous determination of a primary particle size and mass concentrations of fluid-borne particles that includes a measuring arrangement, a mechanism that simultaneously detects a maximum and a temporal progression of a thermal radiation originating from the fluid-borne particles with at least one defined angle or angle range after a pulsed exciting by the measuring arrangement, the mechanism being at least one of adjustable in cross section and variable in diameter, the mechanism being arranged to one of protrude into a fluid and wrap around a fluid, a radiation emitter unit, and a temporally high-resolution optical detector unit.

The mechanism may comprise at least one detector, each detector having one of a photo multiplier and a light sensitive semiconductor. The optical sensor unit may further comprise a voltage source, at least one spectral filter. The optical sensor unit may further comprise at least one of an imaging optic and a light guiding fiber optic. The optical sensor unit may further comprise a fixed adjusted fiber optic. The optical sensor unit may be adapted to be integrated at or in an exhaust stream of a combustion system. The optical sensor unit may further comprise a detector for a simultaneously detecting an elastic scattering signal in at least one defined angle. The optical sensor unit may further comprise a device for the simultaneous detection of a turbidity of the fluid-borne particles. The device may comprise a radiation emitter and a detector arranged opposite the radiation emitter, whereby the device is adapted to calibrate at least one of a mass and a volume concentration of the fluid-borne particles. The optical sensor unit may further comprise a measuring device for simultaneously determining a gas temperature. The fluid may comprise one of a standing fluid and a flowing fluid.

The invention also provides for an optical sensor unit for determining and characterizing fluid-borne particles, that includes a radiation emitting unit and an optical detector unit for determining at least one of a primary particle size and a mass concentration. The optical detector unit being arranged to determine a thermal radiation originating from the fluid-borne particles after a pulsed exciting is determined by the optical detector unit in a direction precisely opposite to that in which the pulsed exciting occurs.

The optical detector unit may comprise at least one of a spectrally selective optical unit and a spatially selective optical unit. The optical detector unit may comprise at least one detector, each detector having one of a photo multiplier and a light sensitive semiconductor. The optical sensor unit may further comprise a voltage source, at least one spectral filter. The optical sensor unit may further comprise at least one of an imaging optic and a light guiding fiber optic. The optical sensor unit may further comprise a fixed adjusted fiber optic for exciting or detection. The optical sensor unit may be adapted to be integrated at or in an exhaust stream of a combustion system. The optical sensor unit may further comprise an additional detector integrated for a simultaneous detection of an elastic scattering signal in at least one defined angle. The optical sensor unit may further comprise a device for the simultaneous detection of a turbidity of the fluid-borne particles. The device may comprise a radiation emitter and a detector arranged opposite the radiation emitter, whereby the device is adapted to calibrate at least one of a mass and a volume concentration of the fluid-borne particles. The optical sensor unit may further comprise a measuring device for simultaneously determining a gas temperature.

The invention also provides for a process for simultaneous determining a mass concentration and one or more parameters of a primary particle size distribution function of fluid-borne particles, wherein the method includes subjecting the fluid-borne particles to pulsed excitement, determining simultaneously a maximal signal value and a time signal decay of a thermal radiation originating from the fluid-borne particles after the pulsed excitement, the determining being performed within a predetermined time interval, and evaluating the maximal signal value and a time signal decay of a thermal radiation originating from the fluid-borne particles.

The process may further comprise adjusting an experimental signal decay and of a fluid temperature to a theoretical data from a library in order to determine a primary particle size distribution function. The library of theoretical data may be created simultaneously with the evaluating by including theoretical models. The process may further comprise additionally determining an aggregate size simultaneously by evaluating an elastic ray scattering.

The invention still further provides for a device for simultaneous in-situ determination of particle size and mass concentration of fluid-borne particles, wherein the device includes a sensor unit comprising a sending unit and a receiver, a laser coupled to the sensor unit, a detector coupled to the sensor unit, and a microprocessor coupled to the sensor unit, wherein the sensor unit is at least one of adjustable in cross section and variable in diameter and wherein the sensor unit is arranged to one of protrude into the fluid-borne particles and wrap around the fluid-borne particles.

The invention additionally provides for a method of simultaneous in-situ determination of particle size and mass concentration of fluid-borne particles using a device which includes a sensor unit comprising a sending unit and a receiver, a laser coupled to the sensor unit, a detector coupled to the sensor unit, and a microprocessor coupled to the sensor unit, the sensor unit being at least one of adjustable in cross section and variable in diameter and the sensor unit being arranged to one of protrude into the fluid-borne particles and wrap around the fluid-borne particles, wherein the method include placing the sensor unit adjacent a pipe having a gas flow, and simultaneously determining a particle size and a mass concentration of the fluid-borne particles in the gas flow.

Exemplary embodiments of the invention are in the drawings.

DETAILED DESCRIPTION OF THE INVENTION

Figure 1:
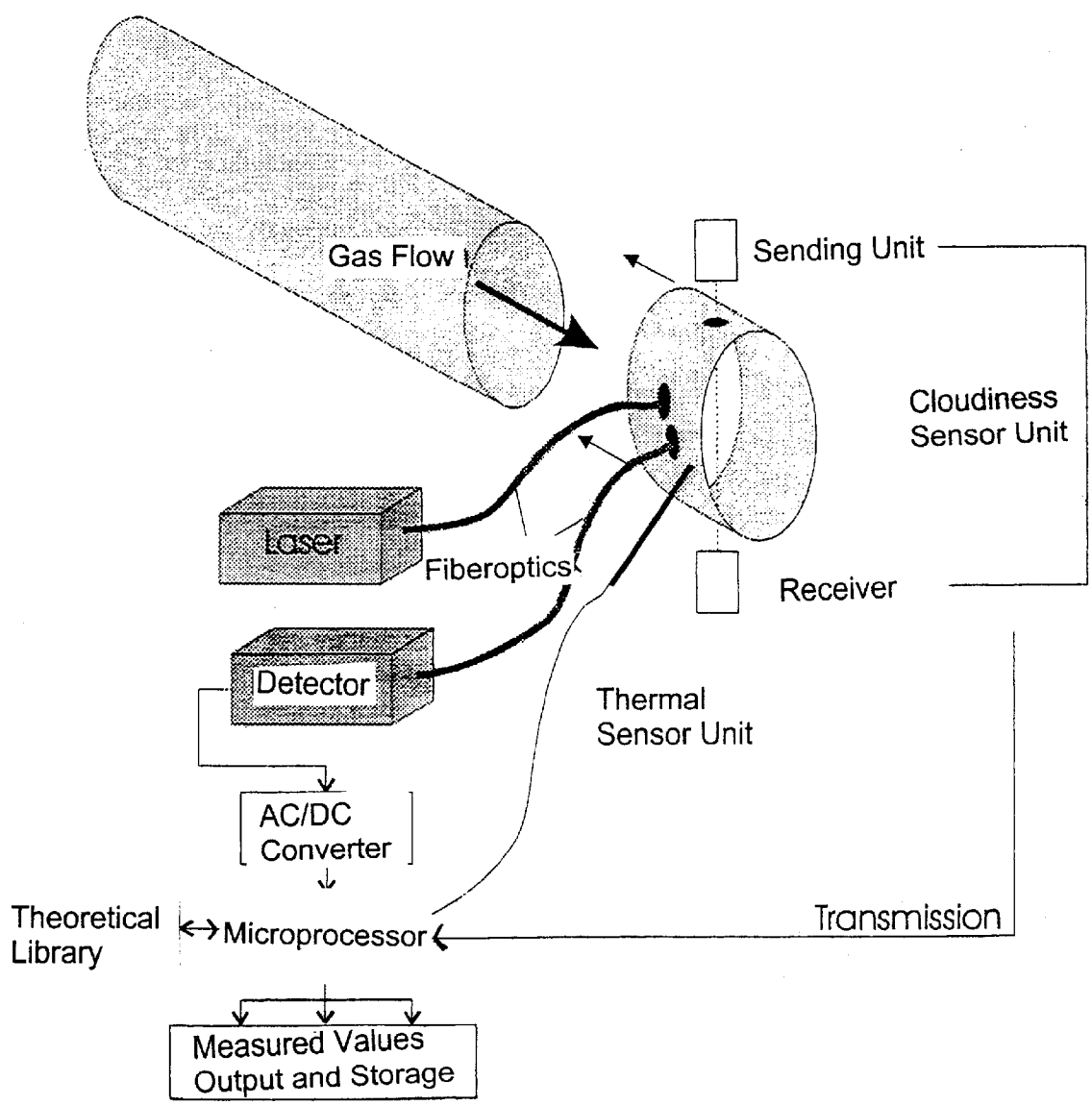
FIG. 1 schematically shows a possible device which allows to determine the particle quantities inside of a pipe without performing modifications to the test object.

FIG. 1 schematically shows a possible device which allows to determine the particle quantities inside of a pipe without performing modifications to the test object. Here, pipe section adjusted in its cross section is mounted such that all features essential for the sensor unit are integrated. Here, introduction and detection occur by way of fiber optics. Additionally, the temperature of the gas stream is measured and fed together with the turbidity value to data processing.

Figure 2:
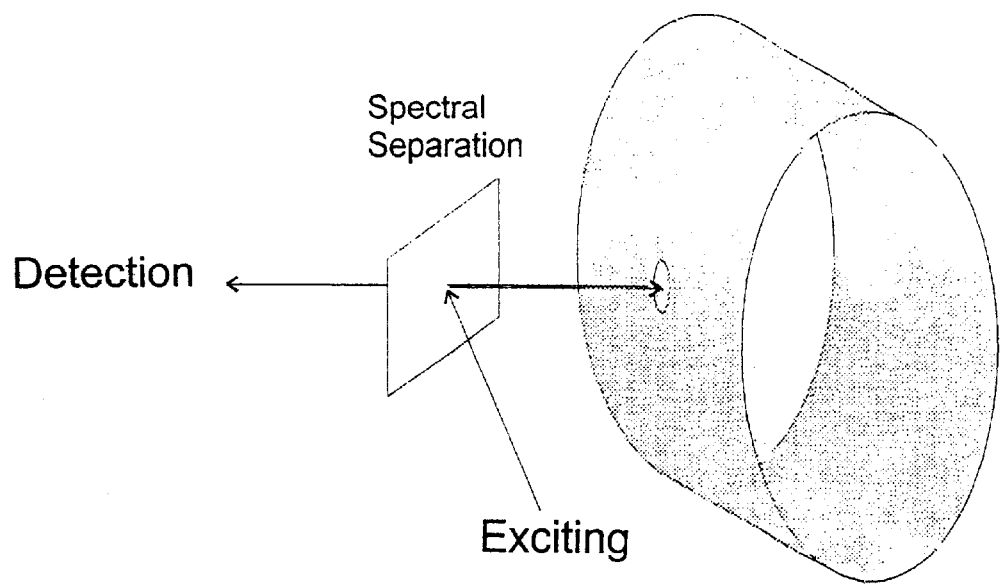
FIG. 2 and FIG. 3 show possible variants which only require a single, small optical access each, with the separation of exciting beam and signal occurring outside of the test object.
Figure 3:
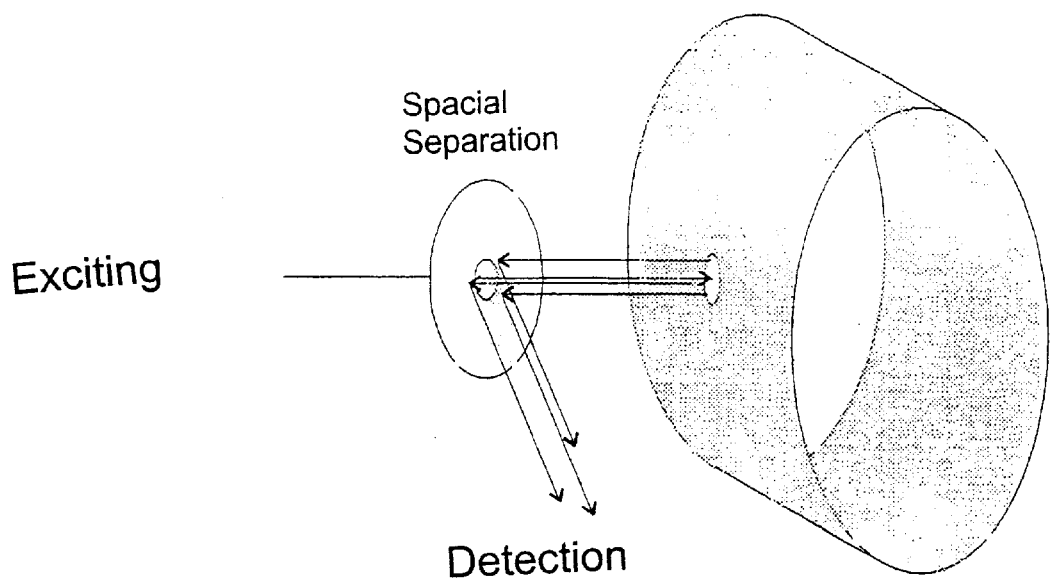

FIG. 2 and FIG. 3 show possible variants which only require a single, small optical access. each, with the separation of exciting beam and signal occurring outside of the test object. In FIG. 2 the separation is performed by the use of a spectrally selective component, such as a holographic mirror, in FIG. 3 by a spatial separation (radiation through a hole inside of a mirror).

What is claimed is:

1. An optical sensor unit for simultaneous determination of a primary particle size and mass concentrations of fluid-borne particles, comprising:
   a measuring arrangement;
   a mechanism that simultaneously detects a maximum and a temporal progression of a thermal radiation originating from the fluid-borne particles with at least one defined angle or angle range after a pulsed exciting by the measuring arrangement;
   the mechanism being at least one of adjustable in cross section and variable in diameter;
   the mechanism being arranged to one of protrude into a fluid and wrap around a fluid;
   a radiation emitter unit; and
   a temporally high-resolution optical detector unit.

2. The optical sensor unit of claim 1, wherein the mechanism comprises at least one detector, each detector having one of a photo multiplier and a light sensitive semiconductor.

3. The optical sensor unit of claim 2, further comprising a voltage source and at least one spectral filter.

4. The optical sensor unit of claim 3, further comprising at least one of an imaging light guiding fiber optic.

5. The optical sensor unit of claim 1, further comprising a fixed adjusted fiber optic.

6. The optical sensor unit of claim 1, wherein the optical sensor unit is adapted to be integrated at or in an exhaust stream of a combustion system.

7. The optical sensor unit of claim 1, further comprising a detector for simultaneously detecting an elastic scattering signal in at least one defined angle.

8. The optical sensor unit of claim 1 further comprising a device for the us detection of a turbidity of the fluid-borne particles.

9. The optical sensor unit of claim 8, wherein the device comprises a radiation a detector arranged opposite the radiation emitter, whereby the device is adapted to calibrate at least one of a mass and a volume concentration of the fluid-borne particles.

10. The optical sensor unit of claim 1, further comprising a measuring device for simultaneously determining a gas temperature.

11. The optical sensor unit of claim 1, wherein the fluid comprises one of a standing fluid and a flowing fluid.

12. An optical sensor unit for determining and characterizing fluid-borne particles, comprising:
    a radiation emitting unit; and
    an optical detector unit for determining at least one of a primary particle size and a mass concentration;
    the optical detector unit being arranged to determine a thermal radiation originating from the fluid-borne particles after a pulsed exciting is determined by the optical detector unit in a direction precisely opposite to that in which the pulsed exciting occurs.

13. The optical sensor unit of claim 12, wherein the optical detector unit comprises at least one of a spectrally selective optical unit and a spatially selective optical unit.

14. The optical sensor unit of claim 12, wherein the optical detector unit comprises at least one detector, each detector having one of a photo multiplier and a light sensitive semiconductor.

15. The optical sensor unit of claim 14, further comprising a voltage source and at least one spectral filter.

16. The optical sensor unit of claim 15, further comprising at least one of an imaging optic and a light guiding fiber optic.

17. The optical sensor unit of claim 12, further comprising a fixed adjusted fiber optic for exciting or detection.

18. The optical sensor unit of claim 12, wherein the optical sensor unit is adapted to be integrated at or in an exhaust stream of a combustion system.

19. The optical sensor unit of claim 12, further comprising an additional detector integrated for a simultaneous detection of an elastic scattering signal in at least one defined angle.

20. The optical sensor unit of claim 12, further comprising a device for the simultaneous detection of a turbidity of the fluid-borne particles.

21. The optical sensor unit of claim 20, wherein the device comprises a radiation emitter and a detector arranged opposite the radiation emitter, whereby the device is adapted to calibrate at least one of a mass and a volume concentration of the fluid-borne particles.

22. The optical sensor unit of claim 12, further comprising a measuring device for simultaneously determining a gas temperature.

23. A process for simultaneously determining a mass concentration and one or more parameters of a primary particle size distribution function of fluid-borne particles, the method comprising:
    subjecting the fluid-borne particles to pulsed excitement;
    determining simultaneously a maximal signal value and a time signal decay of a thermal radiation originating from the fluid-borne particles after the pulsed excitement, the determining being performed within a predetermined time interval; and
    evaluating the maximal signal value and a time signal decay of a thermal radiation originating from the fluid-borne particles.

24. The process of claim 23, further comprising adjusting an experimental signal decay and of a fluid temperature to a theoretical data from. a library in order to determine a primary particle size distribution function.

25. The process of claim 24, wherein the library of theoretical data is created simultaneously with the evaluating by including theoretical models.

26. The process of claim 23, further comprising additionally determining an aggregate size simultaneously by evaluating an elastic ray scattering.

27. A device for simultaneous in-situ determination of particle size and mass concentration of fluid-borne particles, the device comprising:
    a sensor unit comprising a sending unit and a receiver;
    a laser coupled to the sensor unit;
    a detector coupled to the sensor unit; and
    a microprocessor coupled to the sensor unit,
        wherein the sensor unit is at least one of adjustable in cross section and variable in diameter and wherein the sensor unit is arranged to one of protrude into the fluid-borne particles and wrap around the fluid-borne particles.

28. A method of simultaneous in-situ determination of particle size and mass concentration of fluid-borne particles using a device which includes a sensor unit comprising a sending unit and a receiver, a laser coupled to the sensor unit, a detector coupled to the sensor unit, and a microprocessor coupled to the sensor unit, the sensor unit being at least one of adjustable in cross section and variable in diameter and the sensor unit being arranged to one of protrude into the fluid-borne particles and wrap around the fluid-borne particles, the method comprising:
    placing the sensor unit adjacent a pipe having a gas flow; and
    simultaneously determining a particle size and a mass concentration of the fluid-borne particles in the gas flow.

* * * * *